United States Patent [19]

Langner et al.

[11] Patent Number: 4,642,356
[45] Date of Patent: Feb. 10, 1987

[54] FLUOROALKYLSILANES OR SILOXANES, THEIR SYNTHESIS AND USE

[75] Inventors: Jaroslav Langner; Christian Weitemeyer, both of Essen, Fed. Rep. of Germany

[73] Assignee: Th. Goldschmidt AG, Essen, Fed. Rep. of Germany

[21] Appl. No.: 745,258

[22] Filed: Jun. 14, 1985

[30] Foreign Application Priority Data

Jun. 27, 1984 [DE] Fed. Rep. of Germany ....... 3423608

[51] Int. Cl.$^4$ ..................... C07D 307/00; C07F 7/08; C07F 7/10; C07F 7/18
[52] U.S. Cl. .................................. 549/214; 556/413; 556/444; 556/453; 556/456; 556/459; 556/465; 556/479; 556/488; 556/489
[58] Field of Search ................. 549/214; 556/413, 453, 556/456, 444, 459, 488, 489, 465, 479

[56] References Cited

U.S. PATENT DOCUMENTS 2,884,434  4/1959  Smith ............................. 556/465 X
3,994,947 11/1976  Bond et al. ......................... 556/489
4,031,119  6/1977  Ponomareu et al. ............ 556/488 X Primary Examiner—Paul F. Shaver
Attorney, Agent, or Firm—Toren, McGeady and Goldberg

[57] ABSTRACT

New organosilicon compounds of the formula

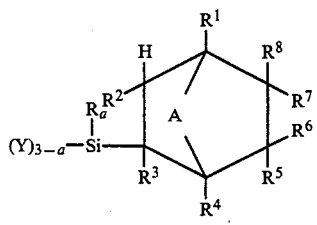

R represents a hydrogen radical with 1 to 6 carbon atoms, or a phenyl radical;

$R^1$, $R^2$, $R^3$ and $R^4$ are the same or different and represent hydrogen or methyl radicals;

$R^5$, $R^6$, $R^7$ and $R^8$ are the same or different and represent hydrogen, fluorine or hydrocarbon radicals with 1 to 8 carbon atoms, or fluorinated hydrocarbon radicals, in which at least one $R^5$, $R^6$ $R^7$ or $R^8$ radicals must be a fluorine or a fluorinated hydrocarbon radical;

Y is a hydrolyzable radical, hydroxyl radical or organosiloxanyl radical;

A represents

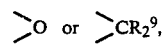

in which $R^9$ may be the same or different and represents a hydrogen or a methyl radical; and
a has a value of 0, 1, 2, or 3.

These compounds can be synthesized by reacting a 2-norbornene derivative of the general formula

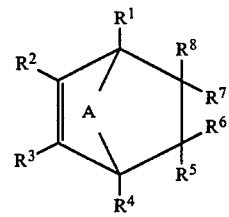

with an organosilicon compound having the formula

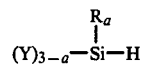

in the presence of a catalyst, known as such for the addition reaction of —SiH to olefinic double bonds, if necessary at an elevated temperature and/or an elevated pressure. They are used to modify the surface of solids, especially of finely divided silica.

14 Claims, No Drawings

FLUOROALKYLSILANES OR SILOXANES, THEIR SYNTHESIS AND USE

BACKGROUND OF THE INVENTION

1. Field of the Invention

The invention relates to new silanes or siloxanes, which have cyclic hydrocarbon radicals with fluorine or fluorohydrocarbon radicals, as well as to their synthesis and use for modifying the surface of solids, especially of finely divided silica.

2. Description of the Prior Art

Silanes or siloxanes which carry fluorine or fluorohydrocarbon radicals, endow the substrates on which they are applied, with water-repellent, oil-repellent, and possibly soil-repellent properties. The compounds are therefore used with success to modify the properties of inorganic or organic materials. Examples of such materials are building materials, such as, plaster, cement, mortar or shaped building materials, such as, tiles of clay or other porous materials, plaster boards, and prefabricated concrete components.

A further application of fluorine-containing silanes or siloxanes is in the modification of pigments and fillers, the modified form of which has improved compatibility with various organic media. This is shown, for example, in the greater ease of incorporating pigments into vehicles and in the reduced tendency of such pigments to separate and deposit. A modified, finely divided silica, especially one that has been pyrogenically produced, improves the suspension behavior of pigments, changes the thixotropy and decreases the evolution of gas from zinc dust paints.

Further possible applications are in the paper industry in which the products can be applied to the paper pulp in the manufacture of the paper, as well as to the already consolidated, still moist paper web or the finished paper. Fluoroorganosilicon compounds are furthermore suitable for treating textile materials, which may be present in the form of fibers or yarns, as woven or knitted materials, or in the form of a nonwoven fabric.

The synthesis of these compounds, however, creates difficulties. The preferred starting materials for synthesizing siloxanes with fluorinated hydrocarbon radicals by methods of the state of the art are silanes, which carry these fluorohydrocarbon radicals. The reason for this lies in the fact that the addition of fluoroalkylolefins to the SiH groups of silanes is facilitated by the presence of halogen atoms that are linked to the same silicon atom. However, the synthesis of siloxanes of the given structure from silanes with fluorinated hydrocarbon groups also creates difficulties, since these silanes, when hydrolyzed and condensed, preferably form cyclic siloxanes.

If, however, fluorinated hydrocarbons with olefinic double bonds are to be added to the SiH group of hydrogen siloxanes, it can be observed that this addition reaction is considerably more difficult, if there are other hydrocarbon or siloxy group substituents on the silicon atom.

The task of introducing fluorinated hydrocarbon radicals in a simple manner in siloxanes of a given structure in order to obtain compounds whose properties can be adjusted by the structure of the siloxane and by the special properties of the fluorinated hydrocarbon groups to meet the requirements of a particular application, has not yet been accomplished satisfactorily by the methods known to the art.

SUMMARY OF THE INVENTION

We have discovered that fluorine-containing hydrocarbon radicals can be introduced in a simple manner into organosilicon compounds, when norbornene derivatives or their 7-oxa derivatives, in which fluorine or fluorohydrocarbon radicals are introduced, are reacted with organosilicon compounds which contain SiH groups.

The compounds thus obtained are novel organosilicon compounds having the formula

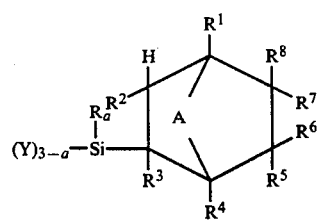

I

With respect to the substituents $R^1$ to $R^8$, formula I is not limited to a specific spatial structure, but comprises all stereoisomeric formulas.

The superscripts and subscripts in the above formula have the following meaning:

R may be the same or different and is a hydrocarbon radical with 1 to 6 carbon atoms or a phenyl radical;

$R^1$, $R^2$, $R^3$, and $R^4$ may be the same or different and are hydrogen or methyl;

$R^5$, $R^6$, $R^7$, and $R^8$ may be the same or different and may be hydrogen, fluorine, hydrocarbon radicals with 1 to 8 carbon atoms, and fluorinated hydrocarbon radicals with the proviso that at least one of $R^5$, $R^6$, $R^7$ or $R^8$ must be fluorine or a fluorinated hydrocarbon radical;

Y is a hydrolyzable radical known to the art, which is linked directly to the silicon atom, a hydroxyl or an organosiloxanyl;

A is a divalent hydrocarbon radical or an oxygen radical; and a is a whole number and is 0, 1, 2 or 3.

A further object of the invention comprises a process for synthesizing the new organosilicon compounds comprising reacting in the presence of a known catalyst for the addition of —SiH to olefinic double bonds, and, if necessary, at an elevated temperature and/or an elevated pressure, a 2-norbornene derivative of the general formula:

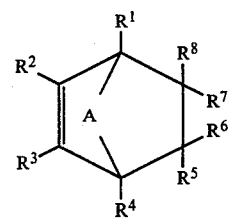

II with an organosilicon compound of the formula

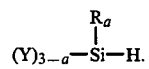

The compounds of formula II are obtainable in a known manner involving the Diels-Alder reaction from cyclopentadienes or furanes and F-substituted olefins.

DESCRIPTION OF THE PREFERRED EMBODIMENTS

In formula I, R preferably may be an aliphatic hydrocarbon radical, such as, the methyl, ethyl, propyl, butyl, or hexyl radical. More preferably, the R radical represents a methyl or phenyl radical, the methyl radical being especially preferred. If several R radicals are linked to the silicon atom, they may be different. The R radical may be substituted. $R^5$, $R^6$, $R^7$, and $R^8$, in the case of a higher number of carbon atoms, may be branched as well as linear.

As fluorinated hydrocarbon radicals, the perfluorinated alkyl radicals with 1 to 20 carbon atoms and, preferably, with 1 to 12 carbon atoms, are preferred.

Y is preferably halogen, hydrocarbonoxy, particularly alkoxy, hydrocarboncarboxy, for example, acetoxy, or alkylated amino.

If Y is an organosilicon radical, it may comprise silicon units of different functionality. The organosiloxanyl radical may be linear or branched. The siloxanyl radical may also carry additional groups of formula I, for example,

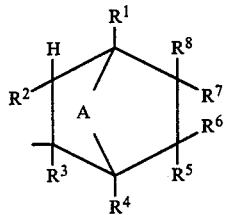

As the divalent hydrocarbon radical in A, the

radical is preferred, in which $R_2^9$ may be the same or different and represents a hydrogen or methyl radical. The bridging group can therefore be

a is a whole number and equal to 0, 1, 2, or 3.

Organosilicon compounds of formula I are preferred in which the substituents have the following meaning
R is a methyl radical;
$R^1$, $R^2$, $R^3$ and $R^4$ are hydrogen and/or methyl radicals;
$R^5$, $R^6$, $R^7$ and $R^8$ are hydrogen, fluorine or hydrocarbon radicals with 1 to 6 carbon atoms, especially aliphatic hydrocarbon radicals or fluorinated, and especially, perfluorinated alkyl radicals with 1 to 20 carbon atoms, in which at least one of the $R^5$, $R^6$, $R^7$ and $R^8$ radicals must be a fluorine or fluoroalkyl radical.

A represents a methylene group or the

group; and
a has a value of 0, 1, or 2.

Especially preferred are organosilicon compounds of formula I in which R represents a methyl radical, $R^1$, $R^2$, $R^3$ and $R^4$ represent a hydrogen radical and $R^5$, $R^6$, $R^7$ and $R^8$ represent a hydrogen radical or the $-C_nF_{2n+1}$ radical. The subscript n is a whole number from 1 to 20. At least one of the $R^5$, $R^6$, $R^7$ or $R^8$ radicals must be a perfluoroalkyl radical.

Typical examples of inventively modified organosilicon compounds are:

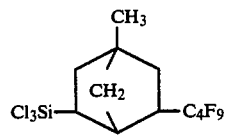

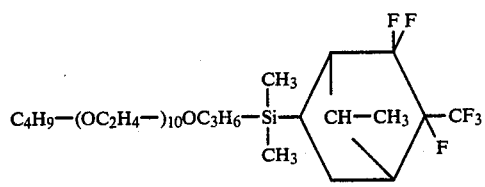

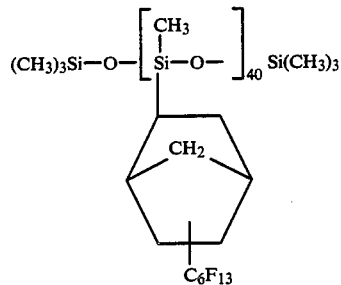

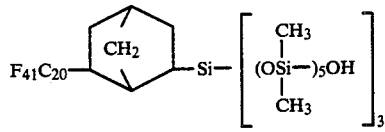

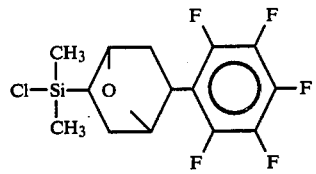

The inventive process can be carried out without the use of solvents. If, however, the organosilicon compound which carries the reactive SiH group is highly viscous because of its molecular weight or its structure, it is advisable to use an inert solvent, such as, toluene. The reaction proceeds at a satisfactory rate at temperatures above 60° C. and especially at 70° to 120° C. The use of a higher pressure is not required, although such a higher pressure may be advantageous for the reaction.

As catalysts, those known from the state of the art for the addition reaction between compounds with olefinic double bonds and SiH groups may be used. Such catalysts are, in particular, platinum catalysts, for example, chlorine-substituted platinum compounds, such as hexachloroplatinic acid.

The inventive compounds not only have the advantage of being easily synthesized, but also have special properties for the modification of the surface of solids, especially of finely divided silica. The methanol number is regarded as a measure of the improved compatibility of the modified silica with organic media or of the incompatibility with water. This methanol number is much higher for the inventive norbornyl derivatives, than for the polysiloxanes, which carry the perfluorinated alkyl radicals directly on the silicon atom. Silica, modified with the inventive compounds, is therefore particularly suitable for incorporation into organic vehicles and for the preparation of defoamers for aqueous systems.

The inventive compounds are, moreover, outstandingly suitable for the surface treatment of building materials, such as, tiles, plaster board and prefabricated concrete components.

The inventive compounds are also particularly suitable for the water, oil, and soil-repellent impregnation of textile materials.

The synthesis and use of the compounds is described in greater detail in the following examples.

EXAMPLE 1

Synthesis of Methyldichlorosilyl-perfluorohexylnorbornane

To a 100 ml 4-neck flask, equipped with reflux condenser with calcium chloride drying tube, thermometer, magnetic stirrer and heating bath, are added 30.9 g of 5-perfluorohexyl-2-norbornene (75 mmoles), a solution of 3 mg of $H_2PtCl_6.6$ $H_2O$ in 1.5 ml of glycol dimethyl ether and 25 ml of toluene. The mixture is heated to 70° C. and 13.0 g of $CH_3HSiCl_2$ (113.2 mmoles) is added dropwise at such a rate, that refluxing is at a minimum (time required: 7 minutes). Refluxing while stirring is continued for a further 3 hours, the temperature increasing during this time from 83° C. to 104° C. Excess $CH_3HSiCl_2$ and toluene are distilled off and the residue of 38.0 g is fractionated under vacuum:

| Fraction I. | 126–144° C./8 torr | 3.7 g |
|---|---|---|
| Fraction II. | 144–148° C./8 torr | 28.0 g |
| Fraction III. | 148–150° C./8 torr | 4.0 g |
| Residue | | 1.6 g |

Gas chromatographic analysis of Fraction II:
Purity: 99.9%
Cl: 13.40%, calculated for

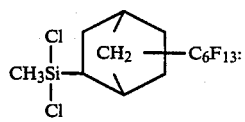

13.47%
$^1H$ NMR (in $CDCl_3$):
$\delta = 0.78$ (s, 3H); $\delta = 1.23$ (t, 1 H);
$\delta = 1.35-2.31$ (m, 6 H) $\delta = 2.40-2.96$ (m, 3 H)

EXAMPLE 2

Synthesis of Bis-1,3-(perfluorohexylnorbornyl)-1,1,3,3-tetramethyldisiloxane

To a 50 ml flask, equipped with reflux condenser, magnetic stirrer and heating bath, are added 8.2 g of perfluorohexyl-2-norbornene and 1.5 mg of $H_2PtCl_6.6$ $H_2O$. The mixture is heated to 65° C. and 1.34 g of 1,1,3,3-tetramethyldisiloxane are then added. This reaction mixture is stirred for 2 hours at 75° C. Gas chromatographic analysis shows the reaction mixture to contain 91.6% of a mixture of isomers of bis-1,3-(perfluorohexylnorbornyl)-1,1,3,3-tetramethyldisiloxane.
Yield of the product, freed from volatile portions under vacuum: 8.4 g (88.4% of the theoretical).

EXAMPLE 3

Synthesis of Poly(perfluorohexylnorbornyl)methylsiloxane of the formula

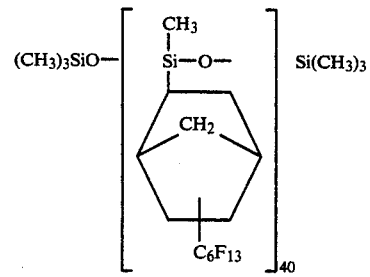

To an apparatus, similar to that described in Example 1, are added 58.1 g of perfluorohexyl-2-norbornene (99.2%, 140 mmoles) and 1 ml of a solution of 4 mg of $H_2PtCl_6.6$ $H_2O$ in 3 ml of glycol dimethyl ether. The mixture is heated to 70° C. and, while stirring, 6.0 g of a polymethyl hydrogensiloxane

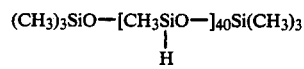

is added dropwise during 35 minutes in such a manner, that the temperature does not exceed 110° C. Further, 1 ml portions of the above catalyst solution are added when half and when all of the siloxane have been added. The reaction mixture is stirred for 3 hours at 100° C. The volatile portions are then removed at 15 torr and 120° C. flask temperature. Yield: 43.7 g of a siloxane, which still contains small residues of SiH. Si: 6.9 weight percent; F: 50.9 weight percent.

EXAMPLE 4

Example 3 is repeated, however using 46 g of benzotrifluoride as the solvent. At the end of the reaction, the benzotrifluoride and other volatile components are distilled off under vacuum of 15 torr up to a flask temperature of 125° C. Yield: 46.5 g of a siloxane with Si: 6.8 weight percent; F: 51.0 weight percent.

EXAMPLE 5

Synthesis of Poly(perfluorododecylnorbornyl)methylsilxoane having the formula

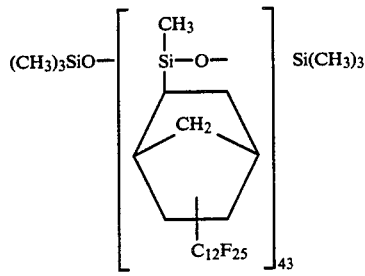

Perfluorododecyl-2-norbornene (99.8 g) is melted in the apparatus described in Example 1 and mixed, while stirring, with 1 ml of a solution of 4 mg of $H_2PtCl_2.6 H_2O$ in 3 ml of diethylene glycol dimethyl ether. A polymethylhydrogensiloxane

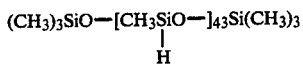

is then added dropwise over the course of 40 minutes. Additional 1 ml portions of the above catalyst solution are added when about half and when all of the siloxane has been added and the reaction mixture is subsequently stirred for 4 hours at 110° to 115° C. The reaction product is dissolved in 100 g of 1,1,2-trichloro-1,2,2-trifluoroethane and poured with stirring into 250 g of acetone. The precipitated product is removed and dried at 100° C. and 1 torr. Yield: 67.3 g of a polysiloxane that contains 4.3 weight percent of Si and 55.9 weight percent of F.

EXAMPLE 6

Synthesis of Polydimethyl-(perfluorohexylnorbornyl-methyl)-siloxane of the average formula

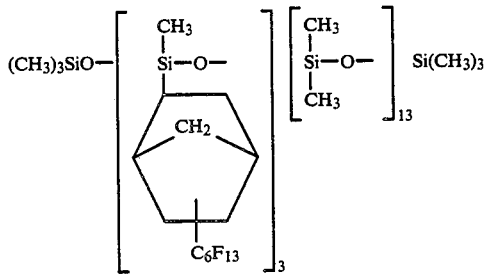

To an apparatus, described in Example 1, are added 20.5 g of perfluorohexyl-2-norbornene (50 mmoles), 3 mg of $H_2PtCl_6.6 H_2O$ in 1.5 ml of glycol dimethyl ether and the mixture is heated with stirring to 60° C. A siloxane (23.2 g) of average formula

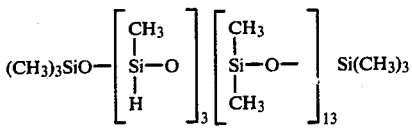

is then added dropwise during 30 minutes. The reaction mixture is stirred for a further 3 hours at 75° C., whereby after a period of 1 hour and 40 minutes, the reaction mixture which originally is not homogenous, becomes homogeneous. The reaction mixture is freed from volatile components under vacuum (130° C. flask temperature at 20 torr). Yield: 39.2 g (89.7% of theoretical).

EXAMPLE 7

Synthesis of Poly-(dodecylmethyl)-(perfluorooctylnorbornylmethyl)-siloxane of average formula

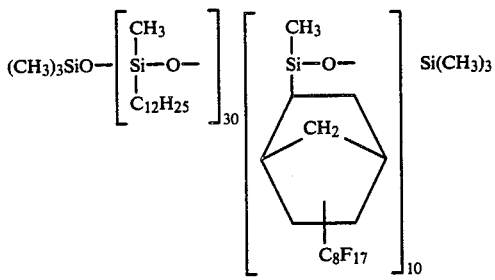

To the apparatus described in Example 1 are added 20.6 g of perfluorooctyl-2-norbornene (50 mmoles) and 3 mg of $H_2PtCl_6.6 H_2O$ in 1.5 ml of glycol dimethyl ether and the mixture is heated with stirring to 60° C. A polysiloxane (12.0 g) of the average formula

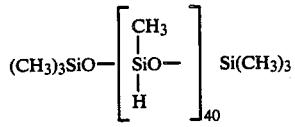

(200 mEq SiH) is added dropwise during 10 minutes and the mixture is then stirred for 20 minutes at 65° C. Subsequently, 26.9 g of 1-dodecene (160 mmoles) are added dropwise. Yield: 56.1 g (97.1% of theoretical) of a polysiloxane of the formula given above.

COMPARISON EXAMPLES (not in accordance with the invention)

I. Attempt to React Perfluorohexylethylene with 1,1,3,3-Tetramethyldisiloxane

To a 50 ml flask, equipped with reflux condenser, magnetic stirrer, thermometer and heating bath, are added 7.0 g of perfluorohexylethylene (20 mmoles) and 1.5 mg of $H_2PtCl_6.6 H_2O$ in 1.5 ml of glycol dimethyl ether. The mixture is heated to 60° C. Subsequently, 1.34 g of 1,1,3,3-tetramethyldisiloxane are added and the mixture is heated for 23 hours at 70° to 75° C. Gas chromatographic analysis reveals that 92% of the perfluorohexylethylene used is present in the unreacted state among various unidentified products.

II. Attempt to React Perfluorohexylethylene with a Polymethylhydrogensiloxane Having the Average Formula

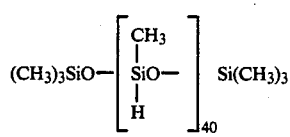

To the apparatus described in Example 1 are added half of a solution of 37.7 g of perfluorohexylethylene in 34 ml of dry tetrahydrofurane and half of a solution of 5 mg of $H_2PtCl_6.6 H_2O$ in 5 ml of tetrahydrofurane. The mixture is stirred for 30 minutes at 7° C. Subsequently, 6.0 g of the above-mentioned polymethylhydrogensiloxane in 11 ml of dry tetrahydrofurane are added dropwise at 23° C. When half of the polymethylhydrogensiloxane has been added, the second half of the perfluorohexylethylene solution and the second half of the catalyst solution are added (time required: 2 hours); the temperature is raised to 35° C. and stirring is continued at this temperature for a further 4 hours. The reaction mixture is then stirred with 1 g of activated charcoal and filtered.

Even before the addition of the activated charcoal, isolated gel particles may be observed. During the filtration of the reaction mixture, there is further gel formation, which completely prevents the filtration.

EXAMPLE 8

(Use of the Inventive Compounds)

To a mixing vessel are added 1,000 g of microdispersed silica with a specific surface area of 200 m²/g and mixed intensively with a solution of 100 g of the compound to be tested in 2,400 g of a suitable solvent. After a mixing time of 1 hour, the solvent is removed during 2 hours at a temperature of 140° to 160° C. and at atmospheric pressure. The microdispersed silica, now free of solvent and coated with the active ingredient, is then heated for a further 2 hours at 180° C. in order to fix the treating agent on the surface. After cooling, the hydrophobicity of the silica is determined by the following method.

Water (50 ml) and 0.2 g of the treated silica are added to an agitated flask and titrated with anhydrous methanol until the whole of the silica is dispersed in the aqueous methanolic phase. The end point of the titration is reached when fewer than 10 visible silica particles are floating on the surface. The methanol number is calculated from the formula.

$$\frac{ml\ CH_3OH \times 100}{50\ ml\ H_2O + ml\ CH_3OH} = \text{methanol number}$$

The methanol number is a measure of the degree of hydrophobicity and is related to the critical wetting tension. Above the critical wetting tension, the treated substance can no longer be wetted completely.

The results are summarized in the following Table.

TABLE

| | Product | Solvent | Methanol Number | Critical Wetting Tension | |
|---|---|---|---|---|---|
| 1 | Dimethylpolysiloxane Viscosity: 50 mPa × sec | methylethyl ketone | 20 | 49 dynes/cm | comparison |
| 2 | methylhydrogenpolysiloxane | methylethyl ketone | 47.4 | 37 dynes/cm | comparison |
| 3 | Trifluoromethylpolysiloxane Viscosity: 1,000 mPa × sec. | methylethyl ketone | 22.5 | 48 dynes/cm | comparison |
| 4 | 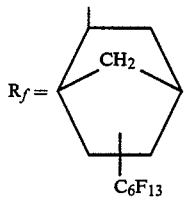 | trichlorotrifluoroethane | 73.7 | 28 dynes/cm | inventive |
| 5 | $\begin{array}{c} CH_3 \\ | \\ Cl-Si-Cl \\ | \\ R_f \end{array}$ | acetone | 70.4 | 30 dynes/cm | inventive |

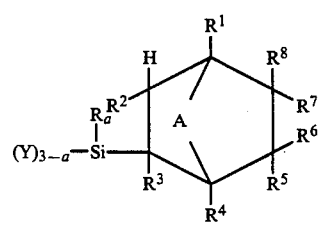

We claim:
1. An organosilicon compound having the formula

$$(Y)_{3-a}-\underset{\underset{R_a^2}{|}}{Si}-A$$

(with ring substituents H, R¹, R⁸, R⁷, R⁶, R⁵, R⁴, R³ around ring A)

R represents a hydrocarbon radical with 1 to 6 carbon atoms, or a phenyl radical;

$R^1$, $R^2$, $R^3$ and $R^4$ are the same or different and represent hydrogen or methyl radicals;

$R^5$, $R^6$, $R^7$ and $R^8$ are the same or different and represent hydrogen, fluorine or hydrocarbon radicals with 1 to 8 carbon atoms, or fluorinated hydrocarbon radicals, in which at least one $R^5$, $R^6$ $R^7$ or $R^8$ radicals must be a fluorine or a fluorinated hydrocarbon radical;

Y is a hydrolyzable radical, hydroxyl radical or organosiloxanyl radical;

A represents $$\diagup\!\!\!\!\diagdown O \text{ or } \diagup\!\!\!\!\diagdown CR_2{}^9,$$

in which $R^9$ may be the same or different and represents a hydrogen or a methyl radical; and a has a value of 0, 1, 2, or 3.

2. The organosilicon compounds of claim 1 wherein R represents a methyl radical, $R^1$, $R^2$, $R^3$ $R^4$ may be the same or different and represent a hydrogen or methyl radical, $R^5$, $R^6$, $R^7$, $R^8$ may be the same or different and represent a hydrogen, fluorine or hydrocarbon radical with 1 to 6 carbon atoms or a fluorinated alkyl, at least one of the $R^5$, $R^6$, $R^7$, $R^8$ having to be a fluorine or fluoroalkyl radical, A represents $$\diagup\!\!\!\!\diagdown CH_2, \diagup\!\!\!\!\diagdown C(CH_3)_2;$$

and a has a value of 0, 1, or 2.

3. The organosilicon compound of claim 2 wherein $R^5$, $R^6$, $R^7$ or $R^8$ is a perfluorinated alkyl radical having 1 to 20 carbon atoms.

4. The organosilicon compounds of claim 1 wherein R represents a methyl radical, $R^1$, $R^2$, $R^3$, $R^4$ represents hydrogen radicals, $R^5$, $R^6$, $R^7$, $R^8$ are the same or different and represent a hydrogen radical or a $C_nF_{2n+1}$ radical, in which n has a value of 1 to 20 and at least one of the $R^5$, $R^6$, $R^7$, $R^8$ radicals is a perfluoroalkyl radical.

5. The compound of claim 1, 2, 3, or 4 wherein Y is halogen, hydrocarbonoxy, hydrocarboncarboxy, or alkylated amino.

6. The compound of claim 5 wherein Y is alkoxy or acetoxy.

7. The compound of claim 1, 2, 3 or 4 wherein Y is a siloxanyl radical carrying a group having the formula

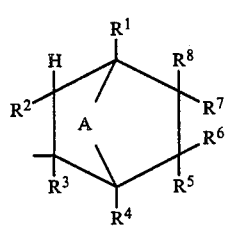

8. A compound selected from the group consisting of

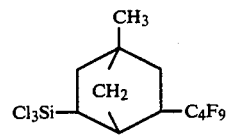

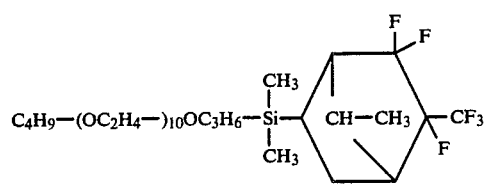

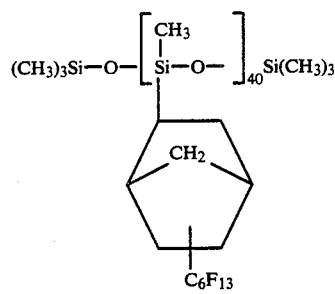

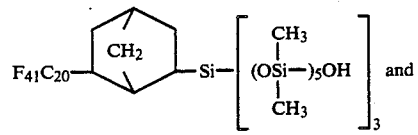

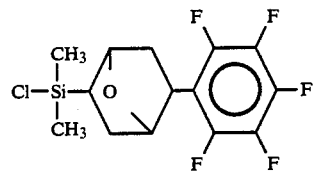

and

9. A process for the synthesis of the compounds of claim 1, 2, 3 or 4 comprising reacting a 2-norbornene derivating having the formula

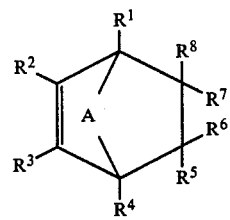

with an organosilicon compound having the formula

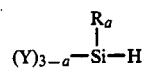

in the presence of a catalyst.

10. The process of claim 9 wherein a chlorinated platinum compound is used as a catalyst.

11. The process of claim 10 wherein the catalyst is $H_2PtCl_6$.

12. The process of claim 9 wherein the reaction is carried out in the presence of an inert solvent.

13. The process of claim 12 wherein the solvent is toluene.

14. The process of claim 9 wherein the reaction is carried out at temperatures of 70° to 120° C.

* * * * *